US008862409B2

(12) United States Patent  
Craddock et al.

(10) Patent No.: US 8,862,409 B2  
(45) Date of Patent: Oct. 14, 2014

(54) METHODS AND APPARATUS FOR MEASURING THE CONTENTS OF A SEARCH VOLUME

(75) Inventors: Ian James Craddock, Bristol (GB); Maciej Bartlomiej Klemm, Bristol (GB); Ralph Benjamin, Bristol (GB)

(73) Assignee: Mi-Crima Limited, Bristol (GB)

( * ) Notice: Subject to any disclaimer, the term of this patent is extended or adjusted under 35 U.S.C. 154(b) by 1198 days.

(21) Appl. No.: 12/741,370

(22) PCT Filed: Nov. 4, 2008

(86) PCT No.: PCT/GB2008/003721  
§ 371 (c)(1),  
(2), (4) Date: Oct. 15, 2010

(87) PCT Pub. No.: WO2009/060182  
PCT Pub. Date: May 14, 2009

(65) Prior Publication Data  
US 2011/0022325 A1       Jan. 27, 2011

(30) Foreign Application Priority Data  
Nov. 5, 2007   (GB) .................................. 0721694.8

(51) Int. Cl.  
*G01N 33/48*   (2006.01)  
*A61B 5/05*    (2006.01)  
*G01S 13/89*   (2006.01)

(52) U.S. Cl.  
CPC ................. *A61B 5/05* (2013.01); *A61B 5/0507* (2013.01); *G01S 13/89* (2013.01)  
USPC .......................................................... 702/19

(58) Field of Classification Search  
CPC .................................................... G01S 7/52046  
USPC ............................................................. 702/19  
See application file for complete search history.

(56) References Cited

U.S. PATENT DOCUMENTS

| 5,920,285 A | 7/1999 | Benjamin |
| 2005/0228279 A1 | 10/2005 | Ustuner et al. |
| 2006/0187754 A1 | 8/2006 | Fink et al. |

FOREIGN PATENT DOCUMENTS

WO   WO-2006/085052   8/2006

OTHER PUBLICATIONS

R. Benjamin, "Synthetic, Post-Reception Focusing in Near-Field Radar," Detection of Abandoned Land Mines, Conference Publication No. 431, pp. 133-137, Oct. 7-9, 1996, © IEE 1996.

(Continued)

*Primary Examiner* — Stephen Cherry  
(74) *Attorney, Agent, or Firm* — Marshall, Gerstein & Borun LLP

(57) ABSTRACT

A method of measuring the contents of a search volume. The method includes: energizing one or more transmitters so as to transmit electromagnetic wave energy into the search volume; detecting the effect of the search volume on the passage of the electromagnetic wave energy by recording two or more signals, each signal being associated with a different propagation path (typically either a monostatic or bistatic path) within the search volume; aligning the signals in order to generate two or more aligned signals which are synthetically focused on a desired voxel in the search volume, each aligned signal being associated with a different propagation path (typically either a monostatic or bistatic path) within the search volume; calculating a quality factor by processing the aligned signals to generate two or more data values, and processing the data values to generate a quality factor, the quality factor being indicative of a degree of coherence in the aligned signals; summing the aligned signals to generate a summed signal; and processing the summed signal to generate an output which is indicative of the internal structure of the search volume at the location of the desired voxel, the output varying in accordance with the quality factor.

16 Claims, 7 Drawing Sheets

(56) References Cited

OTHER PUBLICATIONS

Hollman et al., "Coherence Factor of Speckle From a Multi-Row Probe," 1999 IEEE Ultrasonics Symposium, pp. 1257-1260, © IEEE 1999.

Benjamin et al., "Post-Detection Synthetic Near Field Focusing in Radar or Sonar," Electronics Letters, vol. 35, No. 8, pp. 664-666, Apr. 15, 1999.

LaHaie et al., "Mitigation of Multipath and Ground Interactions in RCS Measurements Using a Single Target Translation," Proc. 23rd Annual Meeting of the Antenna Measurement Techniques Association (AMTA 01), Denver, CO, pp. 411-416, 2001.

Fear et al., "Enhancing Breast Tumor Detection with Near-Field Imaging," IEEE Microwave Magazine, vol. 3, No. 1, pp. 48-56, Mar. 1, 2002.

Fear et al., "Confocal Microwave Imaging for Breast Cancer Detection: Localization of Tumors in Three Dimensions," IEEE Transactions on Biomedical Engineering, vol. 49, No. 8, pp. 812-822, Aug. 2002, © IEEE 2002.

Fear, et al., "Microwaves for Breast Cancer Detection?," IEEE Potentials, pp. 12-18, Feb./Mar. 2003, © IEEE 2003.

Bond et al., "Microwave Imaging via Space-Time Beamforming for Early Detection of Breast Cancer," IEEE Transactions on Antennas and Propagation, vol. 51, No. 8, pp. 1690-1705, Aug. 2003, © IEEE 2003.

Li et al., "An Overview of Ultra-Wideband Microwave Imaging via Space-Time Beamforming for Early-Stage Breast-Cancer Detection," IEEE Antennas and Propagation Magazine, vol. 47, No. 1, pp. 19-34, Feb. 1, 2005.

Shao et al., "UWB Microwave Imaging for Breast Tumor Detection in Inhomogeneous Tissue," Proceedings of the 2005 IEEE Engineering in Medicine and Biology 27th Annual Conference, Shanghai, China, pp. 1496-1499, Sep. 1-4, 2005, © IEEE 2005.

Wang et al., "Time-Delay-and Time-Reversal-Based Robust Capon Beamformers for Ultrasound Imaging," IEEE Transactions on Medical Imaging, vol. 24, No. 10, pp. 1308-1322, Oct. 2005, © IEEE 2005.

Craddock et al., "Development of a Hemi-Spherical Wideband Antenna Array for Breast Cancer Imaging," First European Conference on Antennas and Propagation, EUCAP 2006, pp. 1-5, Nov. 6-10, 2006.

Marr et al., "Bistatic RCS Calculations From Cylindrical Near-Field Measurements—Part II: Experiments," IEEE Transactions on Antennas and Propagation, vol. 54, No. 12, pp. 3857-3864, Dec. 2006.

Klemm et al., "Improved Delay-and-Sum Beamforming Algorithm for Breast Cancer Detection," International Journal of Antennas and Propagation, vol. 2008, Article ID 761402, pp. 1-9, 2008.

International Search Report in International Application No. PCT/GB2008/003721 mailed Mar. 3, 2009.

Written Opinion in International Application No. PCT/GB2008/003721 mailed Mar. 3, 2009.

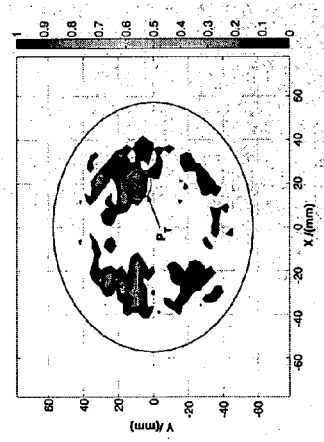
Figure 7a
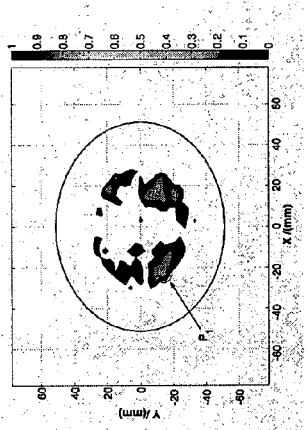
Figure 7b
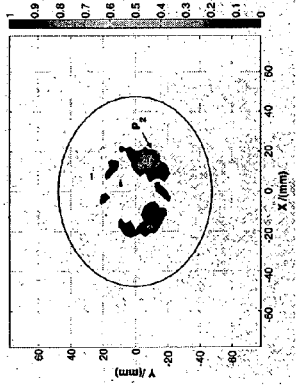
Figure 7c
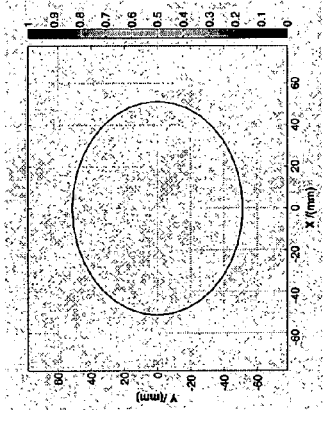
Figure 7d
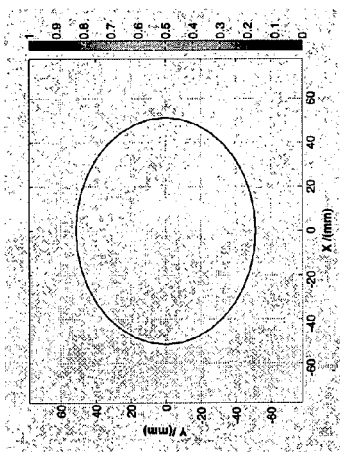
Figure 7e
Figure 7f

METHODS AND APPARATUS FOR MEASURING THE CONTENTS OF A SEARCH VOLUME

FIELD OF THE INVENTION

The present invention relates to a method and apparatus for measuring the contents of a search volume using electromagnetic wave energy.

BACKGROUND OF THE INVENTION

A method of measuring the contents of a search volume using electromagnetic energy is described in U.S. Pat. No. 5,920,285. Individual transmit elements of a transmit array are actuated in turn in order to interrogate the search volume. Reflected signals are recorded, and appropriate phase or time shifts are inserted to simulate, post reception, the shifts that would have occurred if either or both of the transmit and receive array had been focused on the cell using phased array beam steering techniques.

Another method of measuring the contents of a search volume is described in WO 2006/085052 A2. The method includes the steps of: energising one or more transmitters so as to transmit electromagnetic wave energy into the search volume; detecting the effect of the search volume on the passage of the electromagnetic wave energy by recording two or more signals at one or more receivers, each signal being associated with a different transmitter/receiver pair; pre-processing the signals to generate two or more pre-processed signals, each pre-processed signal being associated with a different transmitter/receiver pair; aligning the pre-processed signals in order to generate two or more aligned signals which are synthetically focused on a desired voxel in the search volume, each aligned signal being associated with a different transmitter/receiver pair; and summing the aligned signals to generate an output which is indicative of the internal structure of the search volume at the location of the desired voxel.

Various methods of removing skin surface artefacts are described in WO 2006/085052 A2. However these methods are not effective in removing clutter caused by other effects. These effects include single and multiple reflections from parts of the antenna, its feed, the array structure and the body.

SUMMARY OF THE INVENTION

A first aspect of the invention provides a method of measuring the contents of a search volume, the method including:
a) energising one or more transmitters so as to transmit electromagnetic wave energy into the search volume;
b) detecting the effect of the search volume on the passage of the electromagnetic wave energy by recording two or more signals, each signal being associated with a different propagation path (typically either a monostatic or bistatic path) within the search volume;
c) aligning the signals in order to generate two or more aligned signals which are synthetically focused on a desired voxel in the search volume, each aligned signal being associated with a different propagation path (typically either a monostatic or bistatic path) within the search volume;
d) calculating a quality factor by processing the aligned signals to generate two or more data values, and processing the data values to generate a quality factor, the quality factor being indicative of a degree of coherence in the aligned signals;
e) summing the aligned signals to generate a summed signal; and
f) processing the summed signal to generate an output which is indicative of the internal structure of the search volume at the location of the desired voxel, the output varying in accordance with the quality factor.

The signals which are recorded in step b) and aligned in step c) of the method may comprise raw measured data—that is, unprocessed signals direct from the antennae. Alternatively they may be pre-processed signals which have been pre-processed in some way—for example to reduce or remove unwanted background signals in the raw measured data.

A second aspect of the invention provides apparatus for measuring the contents of a search volume, the apparatus including:
a) an antenna array configured to transmit and receive electromagnetic wave energy to and from the search volume; and
b) a processor configured to:
  i) record two or more signals, each signal being indicative of the effect of the search volume on the passage of the electromagnetic wave energy and being associated with a different propagation path within the search volume,
  ii) align the signals in order to generate two or more aligned signals which are synthetically focused on a desired voxel in the search volume, each aligned signal being associated with a different propagation path within the search volume;
  iii) calculate a quality factor by processing the time-aligned signals to generate two or more data values, and processing the data values to generate the quality factor, the quality factor being indicative of a degree of coherence in the aligned signals;
  iv) sum the aligned signals to generate a summed signal; and
  v) process the summed signal to generate an output which is indicative of the internal structure of the search volume at the location of the desired voxel, the output varying in accordance with the quality factor.

The signals which are recorded and aligned by the processor may comprise raw measured data—that is, unprocessed signals direct from the antenna array. Alternatively they may be pre-processed signals which have been pre-processed in some way—for example to reduce or remove unwanted background signals in the raw measured data.

In one embodiment of the invention described below, each data value is indicative of the energy of one or more of the aligned signals. However each data value may be indicative of other properties, such as:
the amplitude of one or more of the aligned signals;
the amplitude of the spectral content of one or more of the aligned signals at one or more frequencies;
the spectral content of one or more of the time-aligned signals at one or more frequencies; or
the time of arrival of one or more of the time-aligned signals.

The step of calculating the quality factor may include calculating a parameter which is indicative of a degree of statistical dispersion of the data values. This parameter may be for example the standard deviation, variance, range, interquartile range, mean difference, mean absolute deviation, average absolute deviation, or a similar statistical measure of the dispersion of any of the above-mentioned data values.

The step of calculating the quality factor may include calculating a parameter which assesses the total energy of the summed signal relative to the sum of all the energies of the aligned signals. These energies may be computed from the entire signal or from only part of the signal bandwidth if it is desired to emphasize a particular band of the signal.

The step of calculating the quality factor may include generating a series of different summed signals, each different summed signal being generated by summing a different number of the aligned signals; and processing the different summed signals to calculate the quality factor. For instance the different summed signals may be processed to generate a series of different data values (such as energy values); and fitting a curve to the different data values. This may be performed in combination with the parameter which is indicative of a degree of statistical dispersion of the data values, or separately. Note that a different result may be achieved by changing the order of the summation.

Typically the curve is a polynomial curve such as a quadratic curve.

Typically step a) comprises sequentially energising two or more transmitters. The two or more signals can then be sequentially recorded, each signal being associated with a respective one of the transmitters. Alternatively, simultaneous transmission from two or more transmitters may be accomplished if desired, by any suitable multiplexing scheme such as code or frequency multiplexing.

The antennae may be operated monostatically: that is transmitting and receiving at the same antenna. Alternatively or additionally step b) may comprise sequentially or concurrently recording two or more first signals at a first antenna, each first signal being associated with a respective one of the transmitters; and sequentially or concurrently recording two or more second signals at a second antenna, each second signal being associated with a respective one of the transmitters.

Typically the search volume is part of a human or animal body such as a human breast.

Note that the various elements of the method are presented as a series of steps a)-f) but it will be appreciated that these steps may be performed in any order relative to each other, or at the same time. For instance step d) may be performed before or after step e), or at the same time.

Note also that the various elements of the method are presented as distinct steps a)-f) but it will be appreciated that some of these steps may be merged or replaced by an arithmetic equivalent. For instance instead of summing the aligned signals in step e) and then multiplying the summed signal in step f) by the quality factor, the individual aligned signals may each be multiplied by the quality factor before being summed.

In the preferred embodiment below, microwave energy is used to measure the internal structure of a human breast, but in more general terms any frequency of energy may be used, including electromagnetic energy at optical frequencies. Examples include radar imaging of airspace, through-wall radar and imaging of rooms for security applications. Thus the search volume may comprise a discrete object (such as part of a human or animal body) or a more general search volume such as an air or sea space.

BRIEF DESCRIPTION OF THE DRAWINGS

Various embodiments of the present invention will now be described with reference to the accompanying drawings, in which:

FIG. 3 shows detection results for a 10 mm spherical phantom tumour: a) standard Delay And Sum (DAS), b) improved DAS with QF=a.

FIG. 7 shows 2D focusing results for standard and improved DAS algorithms, for different horizontal planes along the Z-axis: a) standard DAS, z=−9, b) standard DAS, z=−27, c) standard DAS, z=−33, d) improved DAS, z=−6, e) improved DAS, z=−27, f) improved DAS, z=−33. The 2D contour plots of FIG. 7 show signal energy on a linear scale, normalised to the maximum in the 3D volume.

DETAILED DESCRIPTION OF EMBODIMENT(S)

Figure 1:
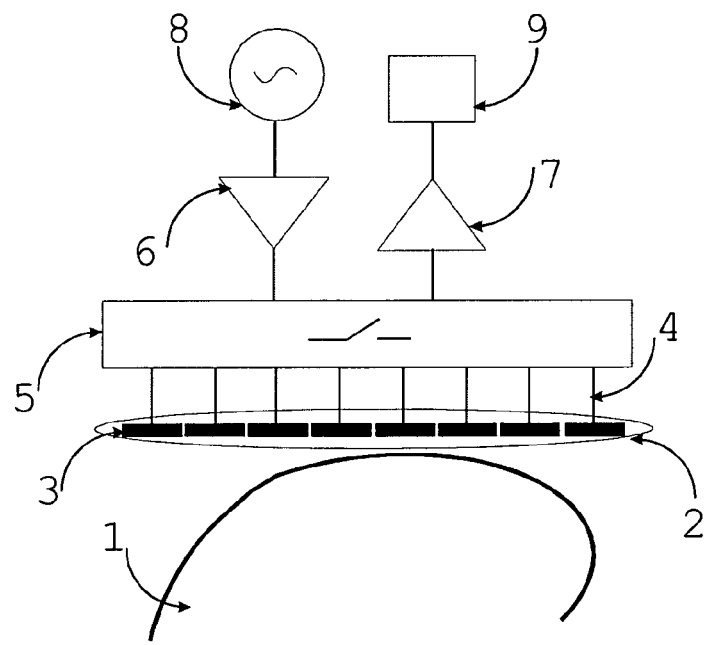
FIG. 1 is a system overview of a breast tumour imaging system.

A real aperture synthetically organised radar for breast cancer detection shown in FIG. 1 operates by employing an array 2 of N antennas (e.g. 3) close to, or in contact with, the breast 1. Each antenna is energised in turn to transmit a pulse of electromagnetic wave energy into the breast 1, and the effect of the breast on the passage of the electromagnetic wave energy is detected by receiving reflected signals $y_i(t)$ at each of the other antennas and recording the signals $y_i(t)$. Thus each signal $y_i(t)$ is associated with an $i^{th}$ transmitter/receiver pair of antennas, and consequently with a different propagation path within the breast 1. The pulse generator 8 and the detector 9 may be time-shared, by means of a switching matrix 5 as shown in FIG. 1, as may any transmit or receive path amplification (6, 7).

The detector 9 includes a processor configured to perform various signal processing steps described below. The first step of signal processing deals with the reduction or elimination of unwanted background signals in the raw measured data. This process must be performed before equalisation and 3D focusing algorithms will be applied. When a mono-static synthetic aperture radar is used for breast cancer detection, tumour extraction aims at removing strong skin reflection from measured data. This is usually performed by simple subtraction from the averaged skin reflection signal (see E. Fear, X. Li, S. C. Hagness, and M. Stuchly, "Confocal microwave imaging for breast cancer detection: Localization of tumors in three dimensions," IEEE Transactions on Biomedical Engineering, vol. 49, no. 8, pp. 812-822, August 2002) or by more sophisticated algorithms as presented in E. J. Bond, X. Li, S. C. Hagness, and B. D. Van Veen, "Microwave imaging via space-time beamforming for early detection of breast cancer," IEEE Transactions on Antennas and Propagation, vol. 51, no. 8, pp. 1690-1705, August 2003.

The approach used in the system of FIG. 1 to reduce or remove unwanted background signals is different. In the multi-static real aperture array 2, the measured response contains not only strong skin reflections, but also reflections from other mechanical parts of the array as well as antenna coupling signals. All these undesired signals are usually of greater amplitude than the tumour response. To subtract all unwanted signals, the antenna array 2 is physically rotated and a second radar measurement is performed. This target displacement method is commonly used in radar cross-section measurements to subtract undesired signals. See for example:

R. A. Marr, U. H. W Lammers, T. B. Hansen, T. J. Tanigawa, R. V. McGahan, "Bistatic RCS Calculations From Cylindrical Near-Field Measurements—Part II: Experiments", IEEE Transactions on Antennas and Propagation, Volume 54, Issue 12, Dec. 2006 Page(s):3857-3864; and I. J. LaHaie and M. A. Blischke, "Mitigation of multipath and ground interactions in RCS measurements using a single target translation", in Proc. 23$^{rd}$ Annual Meeting of the Antenna Measurement Techniques Association (AMTA 01), Denver, Colo., 2001, pp. 411-416.

Rotation gives two sets of measured data, in which undesired signals such as antenna coupling, or skin reflections are almost identical and appear at the same time position, therefore they can be eliminated. In contrast, a tumour response will appear at different time positions in these two measured sets (unless it is on the axis of rotation). Applicability of this technique will depend on the homogeneity of the breast within a given angle defined by rotation. It is therefore assumed that within the angle of array rotation: a) the distance between the antennas 2 and the skin remains unchanged, b) skin properties and thickness is the same, c) normal breast tissue properties do not change.

Before applying the focusing algorithm described below, a pre-processing step is normally performed. This process aims at equalisation of scattered tumour responses for different antenna pairs. Ideal pre-processing would result in all received pulses being of the same shape, amplitude and perfectly time-aligned. In pre-processing the following steps are performed: 1. reduction or elimination of background signals, by subtraction, from measured data, 2. equalisation of tissue losses, 3. equalisation of radial spread of the spherical wavefront, 4. removal of skin artefacts as described in WO 2006/085052 A2. In the description below for simplicity we do not account for the frequency-dependence of the tissue losses nor for the frequency-dependent radiation patterns of the antennas.

Delay-and-sum (DAS) beamforming is a basic and well known method. See for example:

Wenyi Shao; Beibei Zhou; Zhaowen Zheng; Gang Wang; "UWB Microwave Imaging for Breast Tumor Detection in Inhomogeneous Tissue", 2005. IEEE-EMBS 27th Annual International Conference of the Engineering in Medicine and Biology Society, Page(s):1496-1499

W. Zhisong, L. Jian, W. Renbiao; "Time-delay- and time-reversal-based robust capon beamformers for ultrasound imaging", IEEE Transactions on Medical Imaging, Volume 24, Issue 10, Oct. 2005 Page(s):1308-1322.

First the pre-processing steps described above are performed, optionally including removal of skin artefacts in step 4. Next, appropriate time-delays $T_i$ for all received signals are computed. The time-delay $T_i$ for a given transmitter/receiver pair is calculated based on the antennas' positions, the position of the focal point r=(x; y; z) as well as an estimate of average wave propagation speed, which in the present case is simply assumed to be constant across the band.

Essentially, the scattered energy at a given focal point within the breast volume can be expressed as:

$$F_r(x, y, z) = \int_0^\tau \left( \sum_{i=1}^{M} w_i(x, y, z) y_i(t - T_i(x, y, z)) \right)^2 dt \quad (1)$$

where: M=N(N−1)/2 (N is the number of antennas in the array), $w_i$ is a location dependant weight calculated during pre-processing, $y_i$ is the measured radar signal; and $T_i$ is the time-delay along the bistatic path to the location (x, y, z).

During image formation, the focal point moves from one position to another within the breast. At each location all time-shifted responses are coherently summed and integrated. Integration is performed on the windowed signal, the length of the integration window being chosen according to the system bandwidth. A three-dimensional (3D) map of scattered energy is formed in this way. The main advantage of the DAS algorithm is its simplicity, robustness and short computation time.

The improved DAS algorithm uses an additional weighting factor QF (quality factor), compared to the standard DAS expressed in equation (1) above. QF can be interpreted as a quality factor of the coherent focusing algorithm. In one possible implementation it is calculated in three steps. Firstly, for each focal point, a curve of cumulative energy collection is plotted during the coherent signal summation. An example of such a measured curve at a focal point containing a tumour response is presented in FIG. 2.

Figure 2:
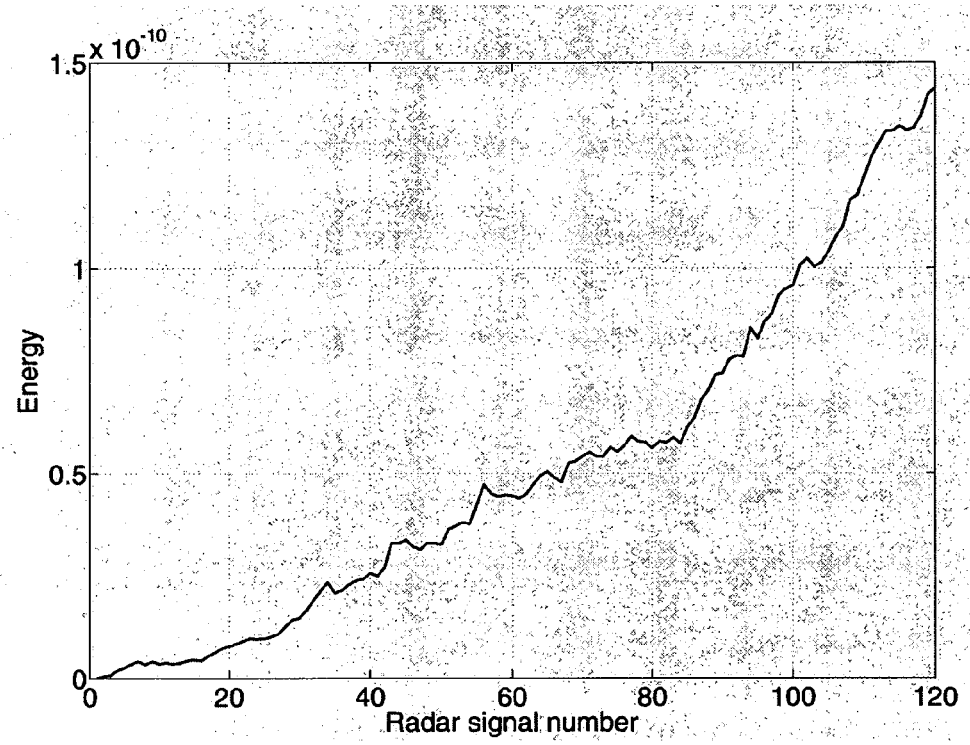
FIG. 2 shows an example of a curve of energy collection data values.

The X-axis of the curve in FIG. 2 represents a respective value for M in equation (1) above, and the Y-axis represents $F_r(x,y,z)$ for that value of M. In other words, the first data value forming the curve (where M=1) represents the energy from one transmitter/receiver pair only, the mid-point (where M=60) represents the energy from a sum of the signals from half of the transmitter/receiver pairs, and the last data value (where M=120) represents the energy from a full summation of the signals from all transmitter/receiver pairs. Thus this last data value, obtained after summation of all radar signals, is equal to the focused energy $F_r(x,y,z)$ in equation (1) above.

Next, the energy collection curve of FIG. 2 is re-scaled by normalising it to the standard deviation of energy, $\sigma_e$, for all radar signals used in the summation. Normalisation is actually performed using multiplication by $1/(1+\sigma_e)$, since in the ideal case of equal energy in all (equalised) measured radar signals $\sigma_e=0$. This may be thought of as a heuristic scaling of the data to give greater weight to those signals that, following equalisation, more closely resemble the desired case of equal energy. The utility of this heuristic weighting is evident from the results presented in the following sections.

In a last step, the processor estimates the coefficients of a second-order polynomial (y=ax$^2$+bx+c), which is the least-square error fit of the normalised curve of coherent energy collection. The choice of the second-order polynomial comes from the fact that a curve of cumulative energy collection during a perfect coherent signal summation would follow a quadratic curve. Then, the processor assumes that QF=a.

The characteristic equation of the improved DAS algorithm can therefore be expressed as:

$$F_r(x, y, z) = QF(x, y, z) \int_0^\tau \left( \sum_{i=1}^M w_i(x, y, z) y_i(t - T_i(x, y, z)) \right)^2 dt \quad (2)$$

where:
- $y_i(t)$ is $i^{th}$ measured radar signal.
- $\tau$ is the duration of the integration window, which is approximately equal to the reciprocal of the bandwidth.
- $w_i(x,y,z)y_i(t)$ is the pre-processed signal associated with the $i^{th}$ transmitter/receiver pair at time t;
- $w_i(x,y,z)y_i(t-T_i(x,y,z))$ is the time-aligned signal synthetically focused on a desired voxel in the search volume at position x,y,z at time $(t-T_i(x,y,z))$ and associated with the $i^{th}$ transmitter/receiver pair; and
- QF(x,y,z) is the quality factor calculated by processing the time-aligned signals to generate a curve of energy data values as shown in FIG. 2, and processing the curve of energy data values to generate the quality factor QF, the quality factor QF being indicative of a degree of coherence in the aligned signals at the position x,y,z.

Sections A and B below present the experimental results of tumour detection using a curved antenna array and 3D breast phantom. Focusing results for standard DAS algorithm are compared to those for the improved DAS and differences between both algorithms are discussed. Results are presented for tumours of two different sizes and located at different positions: a) 10 mm spherical tumour located at position $P_T$ (x=20, y=20, z=-20), b) 7 mm spherical tumour located at position $P_T$(x=20, y=10, z=-10). All co-ordinates are quoted in mm.

Section A. 10 mm Spherical Phantom Tumour

Figure 3A:
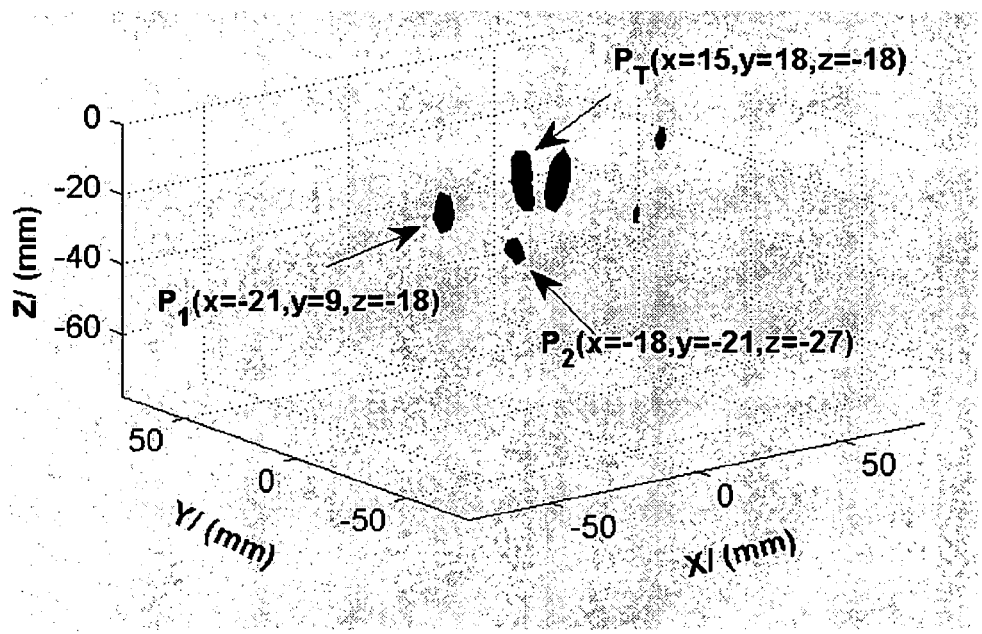
Figure 3B:
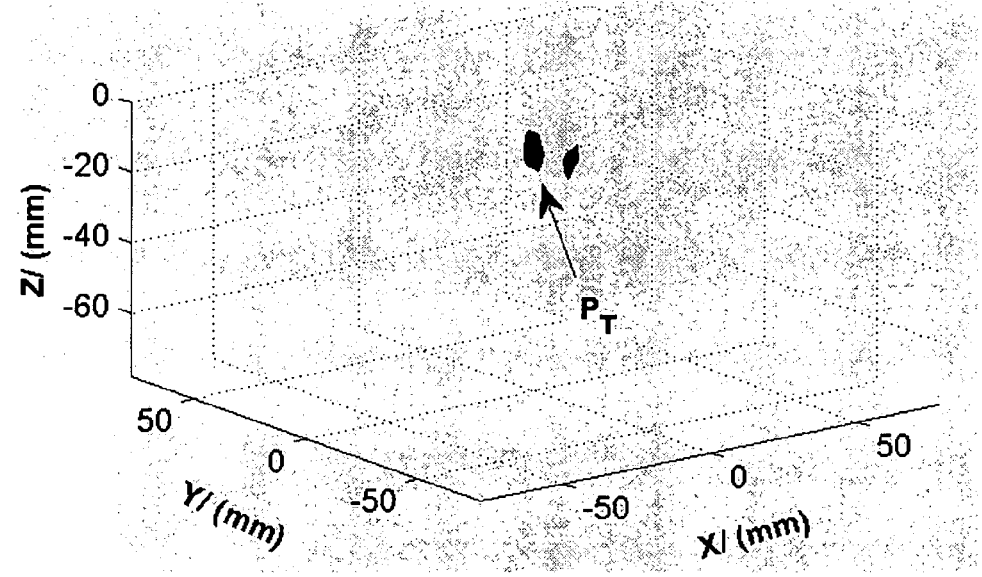
Figure 4B:
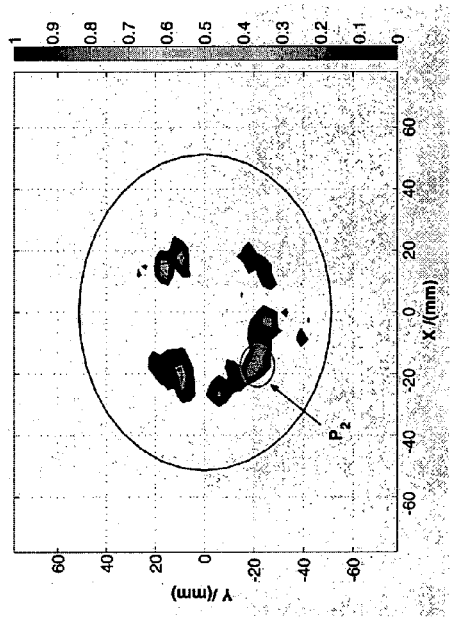
FIG. 4 shows 2D focusing results for standard and improved DAS algorithms, for different horizontal planes along the Z-axis: a) standard DAS, z=−18, b) standard DAS, z=−27, c) improved DAS, z=−18, d) improved DAS, z=−27. The 2D contour plots of FIG. 4 show signal energy on a linear scale, normalised to the maximum in the 3D volume.
Figure 4A:
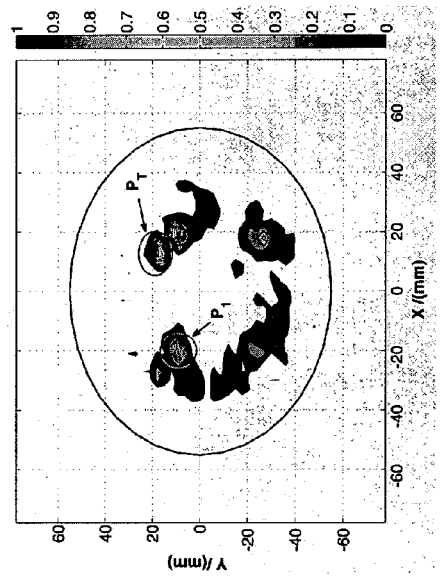

FIGS. 3a and 3b present 3D focusing results for a 10 mm spherical phantom tumour located at the position $P_T$ (x=20, y=20, z=-20). Specifically, these figures present -3 dB contour maps of scattered energy, which is assumed to be indicative of the internal structure of the search volume at the location of the desired voxel at position x,y,z. FIGS. 3a and 3b contrast the outputs of the standard DAS algorithm of equation 1 (FIG. 3(a)) and the improved DAS algorithm of equation 2 (FIG. 3(b)). As can be seen in FIG. 3(a), there are several scatterers present in the image when focusing the standard DAS algorithm. The strongest scatterer within the entire 3D volume is located at position $P_T$ (x=15, y=18, z=-18) and it is associated with a tumour response. FIG. 3a also indicates the locations of two other strong scatterers located at position $P_i$(x=-21, y=9, z=-18) and $P_2$(x=-18, y=-21, z=-27). FIGS. 4(a) and 4(b) present 2D focusing results for standard. DAS on the horizontal planes (Z-axis) containing the $P_T$, $P_1$ (both at z=-18) and $P_2$(z=-27) signals associated with clutter. The 2D contour plots show signal energy on a linear scale, normalised to the maximum in the entire 3D volume. The skin location at each plane is presented as a black circle. From FIG. 4(a) for the plane containing the tumour the focused tumour response ($P_T$) can be relatively easily recognised and the nearby twin tumour response (at x=18, y=9; the twin target response is due to the background subtraction method—mechanical array rotation by 10 degrees). FIG. 4a also shows strong clutter at position $P_1$ and weaker clutter at other positions arising from imperfect background subtraction. FIG. 4(b) presents the 2D focusing result through the plane (z=-27) containing a strong clutter scatterer at $P_2$.

Figure 4D:
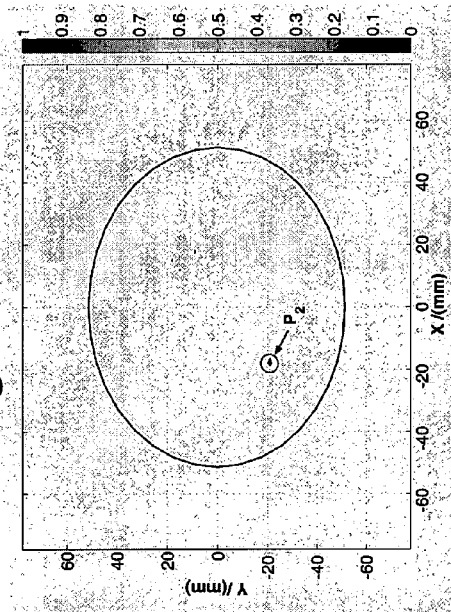
Figure 4C:
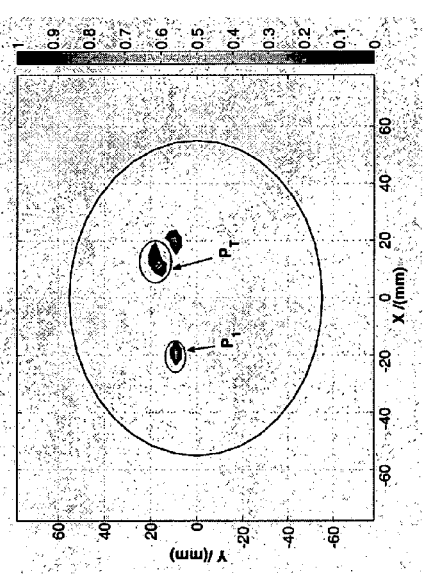

Significantly better detection results are obtained using the improved DAS algorithm presented herein. 3D and 2D focusing results for the improved DAS are presented in FIG. 3(b) and FIGS. 4(c)-4(d). The 3D contour map of scattered energy shown in FIG. 3b contains only the tumour response ($P_T$) and the twin tumour response. Unlike the image of FIG. 3a obtained using standard DAS, there are no other clutter scatterers visible. Signal to clutter ratio, defined as the ratio between energy of the tumour response to the strongest clutter energy within a single 3-D dataset, was improved from 1.25 dB for standard DAS to 3.9 dB for improved DAS (a 2.65 dB improvement).

The same improved performance is observed in the 2D results shown in FIGS. 4(c) and 4(d). As shown in FIG. 4c, in the horizontal plane containing $P_T$, the tumour response clearly stands out and very little clutter exists in the image. As shown in FIG. 4d, in the plane containing $P_2$, clutter is also significantly suppressed. The results shown in FIGS. 3 and 4 show the improved tumour detection of the new DAS algorithm, which uses an additional weight QF, compared to standard DAS.

The following section analyses this particular variant of an improved DAS algorithm and explains why it provides better results. To do so, we will go through all steps of the new algorithm at the three focal points ($P_T$, $P_i$, $P_2$) mentioned earlier. After subtraction of background signals from measured data (by mechanical array rotation), the resultant signals are pre-processed and time-aligned. This initial step is identical for the standard and improved DAS algorithms. Then all pre-processed and time-aligned signals (120 signals for array 2) are coherently summed to give 120 scalar energy quantities.

Figure 5A:
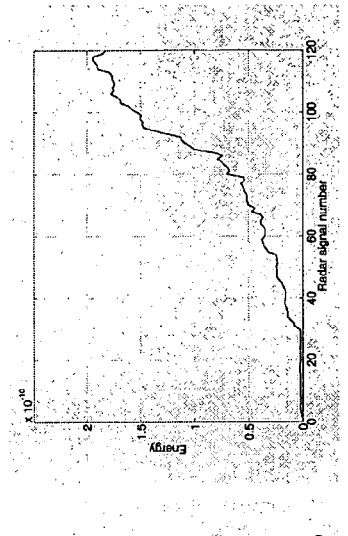
FIG. 5 shows curves of energy collection data values at focal points $P_T$, $P_1$ and $P_2$ (see FIG. 6(*a*)): a) curve for $P_T$ as in standard DAS, a) curve for $P_i$ as in standard DAS, c) curve for $P_2$ in standard DAS, d) curve for $P_T$ as in improved DAS together with the polynomial fitted, e) curve for $P_1$ in the improved DAS together with the polynomial fitted, f) curve for $P_2$ in the improved DAS together with the polynomial fitted.
Figure 5B:
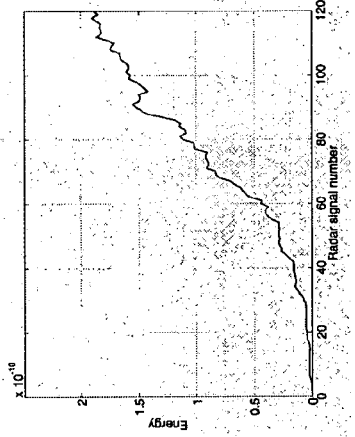
Figure 5C:
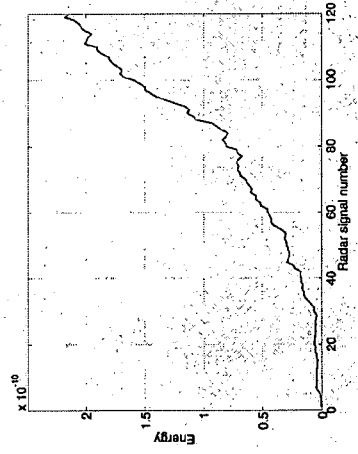

During this process a curve of cumulative energy collection data values is obtained, at each focal point within the focusing volume. This curve is presented in FIG. 5(a), 5(b), 5(c) for focal points $P_T$, $P_1$, $P_2$, respectively. The data values in FIGS. 5a-5c are generated in a similar way to the data values shown in FIG. 2. That is, each data value represents $F_r(x,y,z)$ for a given value of M. If we assume that the focused energy for the tumour location $P_T$ using the standard DAS algorithm is equal to unity $F_s(P_T)=1$, then the focused energy values at focal points $P_1$ and $P_2$ are $F_s(P_1)=0.88$ and $F_s(P_2)=0.85$ respectively. Next, the improved DAS algorithm calculates the standard deviation of energy $\sigma_e$ for all radar signals and re-calculates energy collection curves by normalising them to $\sigma_e$. The rationale to do so is based on the fact that after the initial pre-processing equalisation step, all radar signals should have similar energy.

Figure 5D:
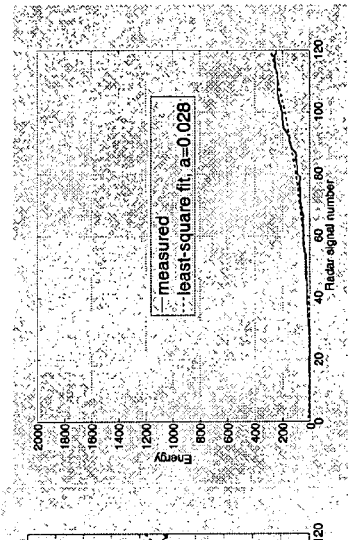
Figure 5E:
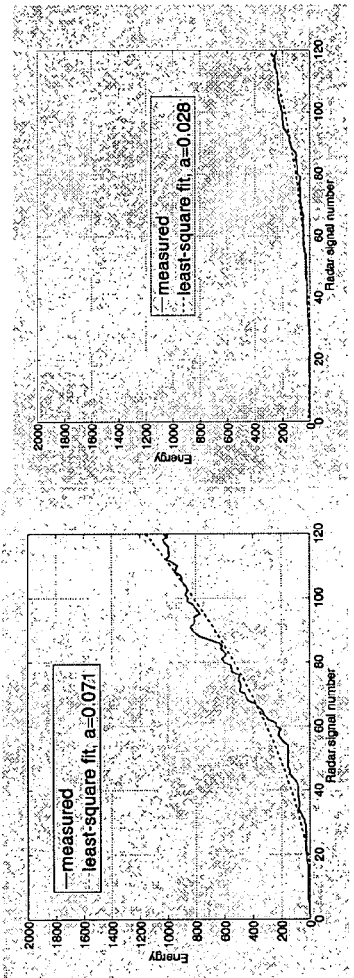
Figure 5F:
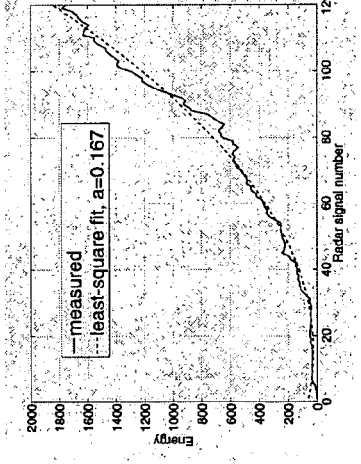

FIGS. 5d-5f (solid curves) show re-scaled (normalised) curves for locations $P_T$, $P_i$, and $P_2$ respectively. It can be observed that, after this normalisation, the results have improved, since the curves for $P_1$, $P_2$ have significantly smaller amplitudes than for $P_T$. Since clutter signals can not be thought as totally uncorrelated, we do not however simply use $\sigma_e$ as the weight factor but apply additional criteria related to the coherent summation of radar signals, as follows.

First, it is assumed that in the ideal case the cumulative energy collection curve should follow a parabola ($y=x^2$). It follows a parabola because e.g. if n in-phase unity-amplitude sinusoids are summed, the resulting sinusoid has an amplitude n. Since the energy is proportional to the square then the energy grows with $n^2$. However a curve containing clutter does not follow a parabola because the sinusoids will not have the same phase. For example if n out-of-phase sinusoids are added, the resulting sinusoid is smaller in amplitude than n. As a further example, if the n+1$^{th}$ signal is in anti-phase to the mean of the previous n signals, it actually results in a reduction of the cumulative energy, rather than an increment.

Therefore, to check the 'quality' of coherent addition of radar signals in the system, the processor performs a second-order polynomial (y=ax²+bx+c) fitting (in the least-square sense) to the measured energy collection curves. This process is performed on the normalised curves. Results of polynomial fitting are shown in FIGS. 5(*d*)-5(*f*) (dashed curve), and the constant a associated with x² equals a=0.167 for $P_T$, a=0.071 for $P_1$ and a=0.028 for $P_2$. Then, assuming that QF=a (see equation 2), the focused energy using improved DAS in this example is: $F_s(P_T)$=1, $F_s(P_2)$=0.38 and $F_s(P_1)$=0.14.

Section B. 7 mm Spherical Phantom Tumour

Figure 6A:
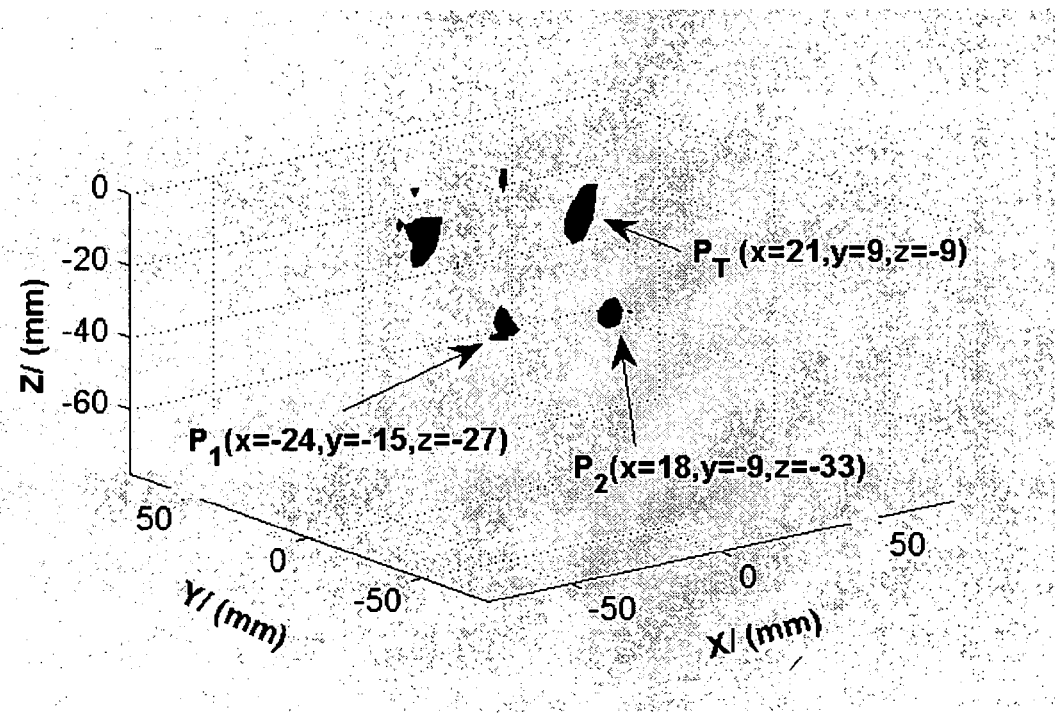
FIG. 6 shows detection results for a 7 mm spherical phantom tumour: a) standard DAS, b) improved DAS with QF=a. 3D figures present −3 dB contour map of scattered energy.
Figure 6B:
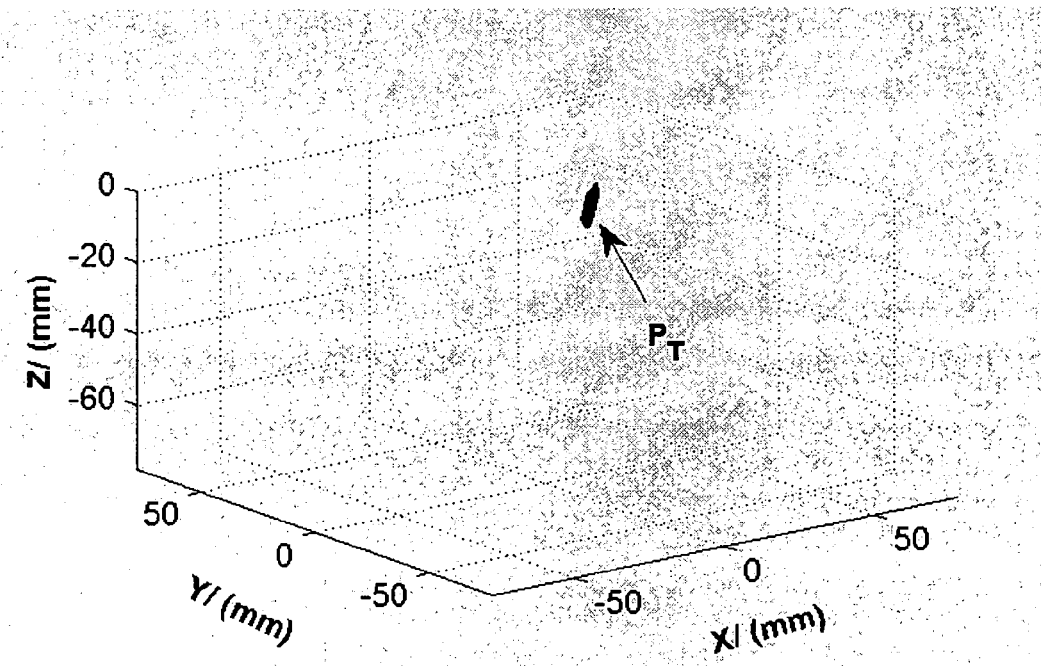
Figure 8C:
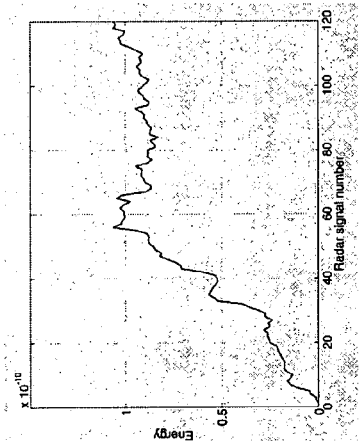
FIG. 8 shows curves of energy collection data values at focal points $P_T$, $P_1$ and $P_2$ (see FIG. 6(*a*)): a) curve for $P_T$ as in standard DAS, a) curve for $P_1$ as in standard DAS, c) curve for $P_2$ in standard DAS, d) curve for $P_T$ as in improved DAS together with the polynomial fitted, e) curve for $P_1$ in the improved DAS together with the polynomial fitted, f) curve for $P_2$ in the improved DAS together with the polynomial fitted.
Figure 8B:
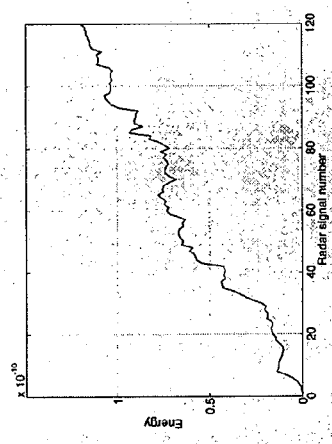
Figure 8A:
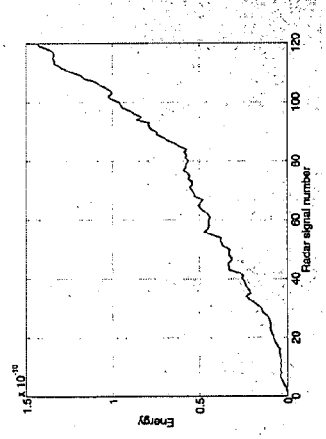
Figure 8F:
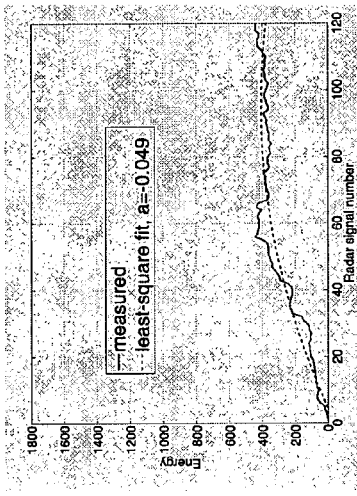
Figure 8E:
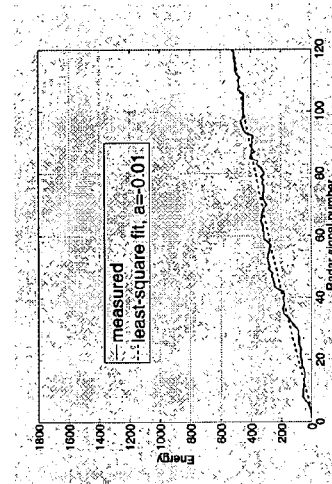
Figure 8D:
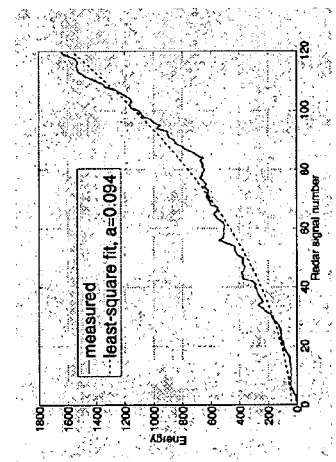

This section presents the detection of a smaller, 7 mm spherical tumour phantom. In FIG. 6 3D focusing results are presented for a 6 mm spherical phantom tumour located at the position $P_T$ (x=20, y=10, z=−10). FIGS. 6*a* and 6*b* present −3 dB contour maps of scattered energy, when focusing was performed using the standard DAS algorithm (FIG. 6(*a*)) and the improved DAS algorithm (FIG. 6(*b*)).

As can be seen in FIG. 6(*a*), by using standard DAS algorithm there are multiple scatterers present in the image. As described previously in Section A for a 10 mm tumour, again the following analysis concentrates on three focal points: a spherical phantom tumour located at $P_T$ (x=21, y=9, z=−6), the strongest clutter scatterer at $P_i$ (x=−24, y=−15, z=−27) and another strong clutter at $P_2$ (x=18, y=−9, z=−33). A significantly better image, with clearly visible tumour scatterer at $P_T$ and no other clutter targets, is presented in FIG. 6(*b*) for the improved DAS algorithm. Signal to clutter ratio was improved from 0.8 dB for standard DAS to 5.2 dB for improved DAS, providing 4.4 dB better performance using the proposed algorithm.

Looking at all 2D focused images for standard DAS, it can be observed that clutter strength generally increases closer to skin. This observation is confirmed when looking at locations of focal points investigated above. In 3D breast phantom the 2 mm skin layer has a radius rskin=59 mm. The true tumour response at $P_T$ is located 35 mm away from the skin ($rP_T$=24 mm), the strongest clutter signal at $P_1$ is 20 mm from the skin ($rP_1$=39 mm) and another strong clutter at $P_2$ is also 20 mm away from the skin ($rP_2$=39 mm). As can be seen, all the strong clutter signals are located closer to skin than the tumour.

In FIG. 8 curves of cumulative energy collection are presented for focal points $P_T$, $P_1$, $P_2$. Plots associated with standard DAS algorithm are shown in FIGS. 8(*a*), 8(*b*) and 8(*c*) for focal points $P_T$, $P_1$, $P_2$, respectively. The value obtained after summation of all radar signals is equal to the focused energy $F_e$ in standard DAS. Next, in the improved DAS algorithm the processor calculates the standard deviation of energy $\sigma_e$ for all radar signals and re-calculates energy collection curves by normalising them to $\sigma_e$. The resulting normalised curves for locations $P_T$, $P_1$ and $P_2$ are depicted in FIGS. 8(*d*), 8(*e*) and 8(*f*) (solid curves), respectively.

It can be observed that, after normalisation, the curves for $P_1$, $P_2$ have significantly dropped compared to $P_T$, due to the higher values of standard deviation of the energy content of the radar signals. Next, the processor performs the second-order polynomial fitting on the normalised energy collection curves to obtain the weight factor QF=a. Results of polynomial fitting are shown as dashed curves in FIGS. 8(*d*)-8(*f*). The constant a associated with x² equals a=0.094 for $P_T$, a=0.01 for $P_i$ and a=0.049 for $P_2$. Interestingly, due to a non-coherent signal summation for focal points $P_1$ and $P_2$, a has not only lower absolute value than for $P_T$, but has also negative sign. The focused energy $F_e$ using the improved DAS algorithm (as in equation 2) will become negative for focal points where QF=a<0, additionally improving imaging results.

An alternative arrangement may be obtained by evaluating the quality factor QF as described in equation (3) below:

$$QF(x, y, z) = \frac{\int_0^\tau \left(\sum_{i=1}^M w_i(x, y, z)y_i(t - T_i(x, y, z))\right)^2 dt}{\sum_{i=1}^M \int_0^\tau (w_i(x, y, z)y_i(t - T_i(x, y, z)))^2 dt} \quad (3)$$

Thus in this case the quality factor is calculated by summing the M aligned signals, and generating a first energy data value E1 from the summed signal:

$$E1 = \int_0^\tau \left(\sum_{i=1}^M w_i(x, y, z)y_i(t - T_i(x, y, z))\right)^2 dt \quad (4)$$

summing the energies of the M aligned signals to generate a second energy data value E2:

$$E2 = \sum_{i=1}^M \int_0^\tau (w_i(x, y, z)y_i(t - T_i(x, y, z)))^2 dt \quad (5)$$

and then calculating the ratio E1/E2.

This quality factor can also be seen to be a measure of the degree of coherence in the signals and hence yields similar results to those presented for the improved DAS method above.

Although the invention has been described above with reference to one or more preferred embodiments, it will be appreciated that various changes or modifications may be made without departing from the scope of the invention as defined in the appended claims.

The invention claimed is:

1. A method of measuring the contents of a search volume, the method including:
   energising one or more transmitters so as to transmit electromagnetic wave energy into the search volume;
   detecting the effect of the contents of the search volume on the passage of the electromagnetic wave energy by recording two or more signals, each signal being associated with a different propagation path within the search volume;
   aligning the signals in order to generate two or more aligned signals which are synthetically focused on a desired voxel in the search volume, each aligned signal being associated with a different propagation path within the search volume;
   calculating a quality factor by processing the aligned signals to generate two or more data values, and processing the data values to generate the quality factor, the quality factor being indicative of a degree of coherence in the aligned signals;
   summing the aligned signals to generate a summed signal; and
   processing the summed signal to generate an output which is indicative of the contents of the search volume at the location of the desired voxel, the output varying in accordance with the quality factor.

2. The method of claim 1 where each data value is indicative of the energy of one or more of the aligned signals.

3. The method of claim 1 wherein the step of calculating the quality factor includes calculating a parameter which is indicative of a degree of statistical dispersion of the data values.

4. The method of claim 1 wherein the step of calculating the quality factor includes calculating a parameter which assesses the total energy of the summed signal relative to the sum of all the energies of the aligned signals.

5. The method of claim 4 wherein the energies are computed from only part of the signal bandwidth.

6. The method of claim 1 wherein the step of calculating the quality factor includes generating a series of different summed signals, each different summed signal being generated by summing a different number of the aligned signals; processing the different summed signals to generate a series of different data values; and fitting a curve to the different data values.

7. The method of claim 6 where a different result can be achieved by changing the order of the summation.

8. The method of claim 6 wherein the curve is a polynomial curve.

9. The method of claim 8 wherein the summed signals are proportional to energy and the curve is a quadratic curve.

10. The method of claim 1 wherein the signals recorded in step b) are equalised signals.

11. The method of claim 1 wherein step a) comprises sequentially energising two or more transmitters.

12. The method of claim 11 wherein step b) comprises sequentially recording two or more signals, each signal being associated with a different propagation path within the search volume.

13. The method of claim 1 wherein the search volume is part of a human or animal body.

14. The method of claim 4 wherein the quality factor is calculated by summing the aligned signals; generating a first energy data value from the summed signal; summing the energies of the aligned signals to generate a second energy data value, and calculating the ratio between the two energy data values.

15. The method of claim 1 wherein the signals recorded in step b) are pre-processed signals.

16. Apparatus for measuring the contents of a search volume, the apparatus comprising:
  an antenna array configured to transmit and receive electromagnetic wave energy to and from the search volume; and
  a processor configured to:
  record two or more signals, each signal being indicative of the effect of the search volume on the passage of the electromagnetic wave energy and being associated with a different propagation path within the search volume,
  align the signals in order to generate two or more aligned signals which are synthetically focused on a desired voxel in the search volume, each aligned signal being associated with a different propagation path within the search volume;
  calculate a quality factor by processing the time-aligned signals to generate two or more data values, and processing the data values to generate the quality factor, the quality factor being indicative of a degree of coherence in the aligned signals;
  sum the aligned signals to generate a summed signal; and
  process the summed signal to generate an output which is indicative of the contents of the search volume at the location of the desired voxel, the output varying in accordance with the quality factor.

* * * * *

UNITED STATES PATENT AND TRADEMARK OFFICE
CERTIFICATE OF CORRECTION

PATENT NO. : 8,862,409 B2  
APPLICATION NO. : 12/741370  
DATED : October 14, 2014  
INVENTOR(S) : Ian James Craddock et al.

Page 1 of 1

It is certified that error appears in the above-identified patent and that said Letters Patent is hereby corrected as shown below:

Title Page: Item 73, under "Assignee", in Column 1, delete "Mi-Crima Limited, Bristol (GB)" and insert -- "Micrima Limited, Bristol (GB)" -- therefor.

Signed and Sealed this  
Third Day of November, 2015

Michelle K. Lee  
*Director of the United States Patent and Trademark Office*